(12) United States Patent
Gauthier et al.

(10) Patent No.: US 9,579,388 B2
(45) Date of Patent: Feb. 28, 2017

(54) SYSTEM AND METHOD FOR ALLEVIATING THE APPEARANCE OF SCARS AND/OR SCAR TISSUE

(71) Applicants: Rene Gauthier, Montreal (CA); Claude Marquis, Lachenaie (CA)

(72) Inventors: Rene Gauthier, Montreal (CA); Claude Marquis, Lachenaie (CA)

(*) Notice: Subject to any disclaimer, the term of this patent is extended or adjusted under 35 U.S.C. 154(b) by 684 days.

(21) Appl. No.: 13/689,716

(22) Filed: Nov. 29, 2012

(65) Prior Publication Data

US 2014/0148515 A1    May 29, 2014

(51) Int. Cl.
| *A61K 47/36* | (2006.01) |
| *A61K 9/00* | (2006.01) |
| *A61K 9/70* | (2006.01) |

(52) U.S. Cl.
CPC ............ *A61K 47/36* (2013.01); *A61K 9/0014* (2013.01); *A61K 9/7015* (2013.01)

(58) Field of Classification Search
CPC ..................................................... A61K 47/36
USPC ....................................................... 514/776
See application file for complete search history.

(56) References Cited

U.S. PATENT DOCUMENTS

| 3,972,997 A | 8/1976 | Nakashio et al. |
| 4,265,233 A | 5/1981 | Sugitachi et al. |
| 5,658,592 A | 8/1997 | Tanihara et al. |
| 5,714,368 A | 2/1998 | Nakada et al. |
| 5,722,942 A | 3/1998 | Tanaka et al. |
| 5,770,229 A | 6/1998 | Tanihara et al. |
| 5,989,874 A | 11/1999 | Nakanishi et al. |
| 6,329,343 B1 | 12/2001 | Leung et al. |
| 2003/0086954 A1 | 5/2003 | O'Halloran |
| 2005/0020537 A1* | 1/2005 | Leung ............... A61K 45/06 514/54 |
| 2005/0142152 A1 | 6/2005 | Leshchiner et al. |
| 2009/0047331 A1 | 2/2009 | Kim et al. |
| 2009/0247485 A1 | 10/2009 | Ahmed et al. |
| 2009/0280150 A1 | 11/2009 | Kamen et al. |
| 2010/0166690 A1 | 7/2010 | Masachika |

FOREIGN PATENT DOCUMENTS

| JP | 9216808 | 8/1997 |
| JP | 2004248949 | 9/2004 |
| WO | WO0050095 | 8/2000 |
| WO | WO03026583 | 4/2003 |
| WO | WO2011/044367 | * 4/2011 |

OTHER PUBLICATIONS

Stavrou et al., Aesth Plast Surg, 2010;34:646-651.*

* cited by examiner

*Primary Examiner* — San-Ming Hui

(57) ABSTRACT

A system for alleviating the appearance of scar tissue, said system comprising a combination of two compounds; a first compound having properties that perform skin regeneration; and a second compound having properties that provide a physical barrier adapted to protect scar tissue by insulating it from ambient air while maintaining and protecting said first compound that is combined therewith.

8 Claims, 1 Drawing Sheet

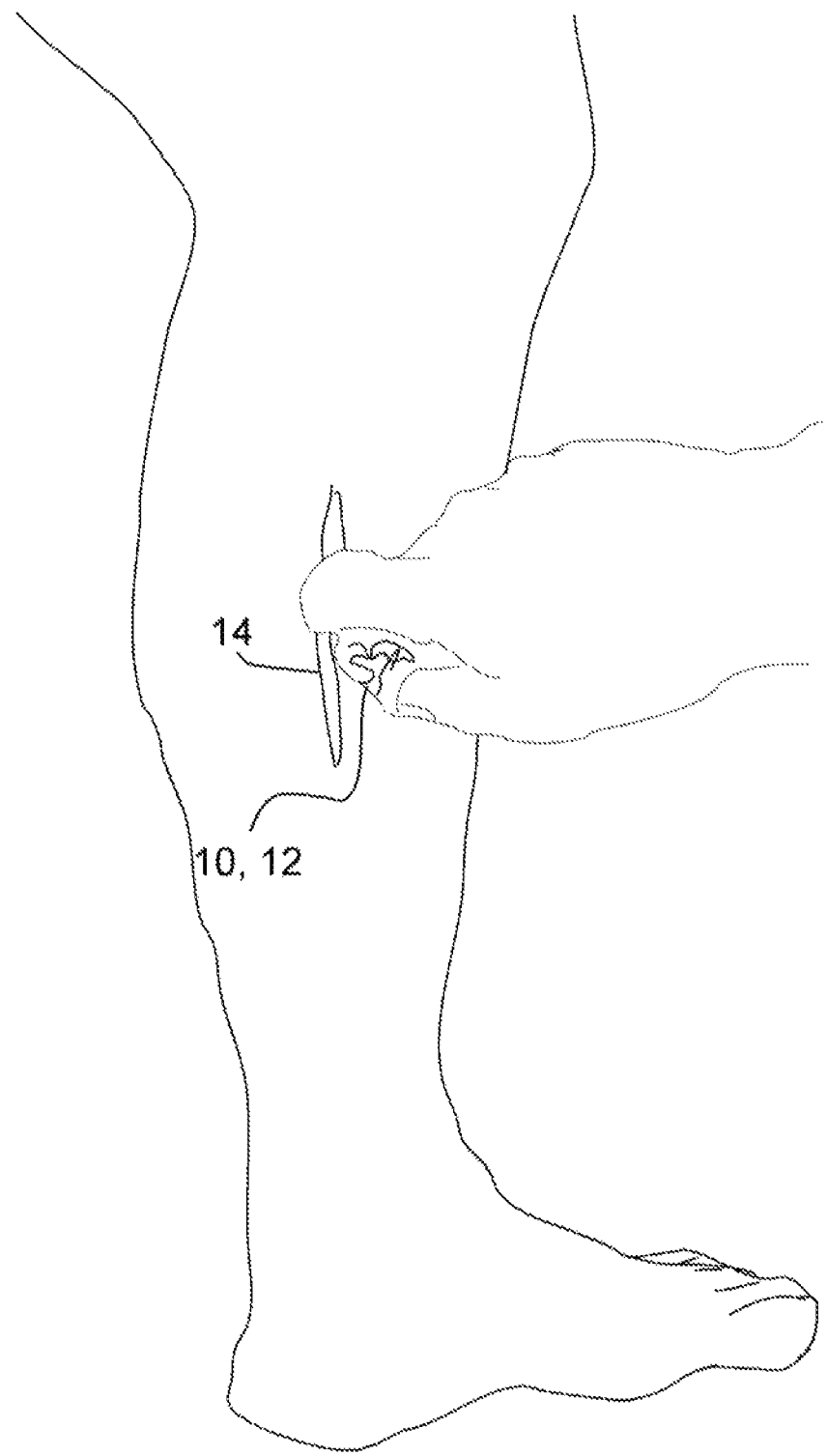

SYSTEM AND METHOD FOR ALLEVIATING THE APPEARANCE OF SCARS AND/OR SCAR TISSUE

FIELD OF THE INVENTION

The present invention relates generally to skin care but more particularly to a system and method for alleviating the appearance of scars and/or scar tissue

BACKGROUND OF THE INVENTION

Scars are not very desirable to most people. Scars can be the result of accidents or surgery, including reconstructive surgery such as for esthetic purposes. Scars or skin lesions can also be caused by a variety of treatments and or skin diseases such as burns, withdrawals of tattoos, laser treatments, dermabrasion, acids, acne cysts, hypertrophic scars, keloids, etc.

Although there have been several techniques, methods and technologies developed over the years to speed up skin regeneration and minimize the look of scars, such as silicone sheets placed over scars to cover a skin treatment compound as well as the skin itself, these techniques—such as silicone sheets—can disintegrate and require help to keep them in place (medical adhesive tape, tailored gauze, etc.), and as such there is no effective system that is easy to implement and which gives excellent results. There is thus a need for improvement.

SUMMARY OF THE INVENTION

In view of the foregoing disadvantages inherent in the known devices now present in the prior art, the present invention, which will be described subsequently in greater detail, is to provide objects and advantages which are:

To provide for an easy and reliable way for speeding up tissue repair and minimizing the appearance of scars.

In order to do so, the invention consists in combining two compounds, a first compound having properties that perform skin regeneration; and a second compound having properties that provide a physical barrier adapted to protect scar tissue by insulating it from ambient air while maintaining and protecting said first compound that is combined therewith.

The first compound is formed as a gel, and includes properties that is adapted to allow a user's skin to become more elastic, and the scar tissue to be more flexible. The second compound is formed as an occluding compound.

The occluding compound is an extracellular bacterial polysaccharide formed from starch.

Preferably, the extracellular bacterial polysaccharide is PULLULAN, formed as a powder that is soluble in water and is adapted to form a film that can be applied as a layer over said first compound when applied to the skin of a user. PULLULAN includes the properties of high adhesion, lubrication, and film forming abilities.

A method of alleviating the appearance of scar tissue comprising the steps of:

a. providing a first compound having properties that perform skin regeneration;

b. applying and massaging the scar tissue with the first compound;

c. allowing the first compound to dry;

d. providing a second compound having properties that provide a physical barrier adapted to protect scar tissue by insulating it from ambient air while maintaining and protecting the first compound;

e. applying the second compound over the top of the first compound;

f. allowing the second compound to dry;

step c. is followed for at least five minutes;

step f. is followed for at least 8 minutes.

Steps d. through f. are followed at least once per day.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter which contains illustrated preferred embodiments of the invention.

BRIEF DESCRIPTION OF THE DRAWINGS

FIG. 1 Schematic side view of the application of a first and or second compound on a scar.

DETAILED DESCRIPTION OF THE PREFERRED EMBODIMENT

A system and method for alleviating the appearance of scars and/or scar tissue consists in the combination of two compounds:

A first compound (10) is a gel that has skin rejuvenation properties, which gives better elasticity to the skin, and allows the scar (14) to be more flexible. The use of this first compound or variants thereof is well known in the art of skin treatment and need not be further discussed herein.

A second compound (12) is an occluding substance, that offers protection from air (oxygen). It consists mainly of pullulan, a well known substance used in the food industry as a food additive in the manufacture of edible films used, for example, in breath freshener strips. Pullulan is an extracellular bacterial polysaccharide produced from starch. As an odorless white colored powder, pullulan is easily soluble in water to make clear and viscous solution. A pullulan film is an oxygen barrier that is 250 times stronger than HPMC film, and 9 time stronger than gelatin. Pullulan is more natural, involving no toxic chemicals. Pullulan is also much more inert than gelatin or HPMC, so there is no interaction with the products it is admixed with. It offers high adhesion, sticking, lubrication, and film forming abilities.

Using pullulan for the use described herein is new and unobvious since the repair of scars is totally unrelated to its use in the food industry.

Instead of using silicon sheets and/or silicon gel, using pullulan gives a superior protection by creating an excellent transparent protective thin film that is invisible and with remarkable adhesive properties. It is also better at creating an impermeable barrier to oxygen than current methods and has a flexible structure made of microfibers that can adapt to all types and shapes of scars. Pullulan is heat stable, biocompatible, non toxic, non-mutagenic, odorless, water soluble and is antistatic.

The two substances can easily be topically applied by the patient at home and requires twice a day applications (morning and evening) on and around the area to be treated.

The method of use on a user goes as follows:

In the morning, apply and gently massage the area with the first compound, that is the skin rejuvenation product. Drying time is about 5 minutes. If it takes more than 8 minutes to dry, this indicates that too much has been applied.

After the first compound has dried, makeup or sunscreen can be applied.

The area to be treated needs to have the first compound constantly for as long as required for full recovery.

Since the first compound is water soluble, washing will remove it completely, ready for the next application whether in the morning or in the evening.

Every evening, apply a thin layer of the first compound and wait a few minutes for it to dry, then apply a very small amount of the second compound over the layer of the first compound. Even if the latter is still a little damp, mixing the two products will not affect the results. It takes from 8 to 12 minutes for the two products to dry, depending on skin type. If it takes over 15 minutes, use a smaller dab of first compound and/or second compound. The second compound—pullulan—must be applied once a day, in the evening only, for continuous occlusive skin repair overnight.

Because the second compound is distributed by way of a pump from a container, it is very clean and sterile. The second compound has exceptional adhesive properties, it is more comfortable and can easily cover all forms of scarring and this, regardless of its location on the body (elbow, knee, face, eyelids, etc.), something the silicone sheets cannot offer. This unobvious combinations, that is a first compound—known in the art of skin repair but heretofore used in combination with various materials such as silicone sheets, etc—along with a second compound which has a new and unobvious use, makes this system and method unique.

| 1 | Purified water (boled) | Aqua | 58.20 |
| 2 | Carbopol 940 | Carbomer | 1.00 |
| 3 | Purified water (boled) | Aqua | 25.00 |
| 4 | Pullulan *MPC | Pullulan | 5.00 |
| 5 | Terra-Pure *Aloe Vera* 200X | *Aloe Barbadensis* Leaf Extract | 0.10 |
| 6 | Zemea Propanediol | Propanediol | 5.00 |
| 7 | Glycerin 99.7% USP | Glycerin | 1.00 |
| 8 | Allantoin | Allantoin | 0.50 |
| 9 | Velsan SC | Sorbitan Caprylate | 1.00 |
| 10 | Mikrokill ECT | Benzyl Alcohol & Salicylic Acid & Glycerin & Sorbic Acid | 1.00 |
| 11 | Chlorophyllin sol. 2.5% | Chlorophyllin-Copper Complex | 0.20 |
| 12 | Sodium Hydroxide, sol. 30% | Sodium Hydroxide | 2.00 |
| 13 | Citric Acid, sol. 50% | Citric Acid | q.s. |

As to a further discussion of the manner of usage and operation of the present invention, the same should be apparent from the above description. Accordingly, no further discussion relating to the manner of usage and operation will be provided.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A method of alleviating the appearance of scar tissue, said method comprising the steps of:
   a. providing a first compound formed as a gel, and includes properties that is adapted to allow a users skin to become more elastic, and said scar tissue to be more flexible and further having properties that perform skin rejuvenation;
   b. applying and massaging said scar tissue with said first compound;
   c. allowing said first compound to dry;
   d. providing a second compound having an occluding compound which provides a physical barrier adapted to protect scar tissue by insulating it from ambient air while maintaining and protecting said first compound;
   e. applying said second compound over the top of said first compound;
   f. allowing said second compound to dry.

2. The method of claim 1, wherein step c. Is followed for at least five minutes.

3. The method of claim 1, wherein step f. is followed for at least 8 minutes.

4. The method of claim 1, wherein steps d. through f. are followed at least once per day.

5. The method of claim 1 wherein said occluding compound is an extracellular bacterial polysaccharide.

6. The method of claim 5, wherein said extracellular bacterial polysaccharide is formed from starch.

7. The method of claim 6, wherein said extracellular bacterial polysaccharide is PULLULAN, wherein said PULLULAN is formed as a powder that is soluble in water and is adapted to form a film that can be applied as a layer over said first compound when applied to the skin of a user.

8. The method of claim 7, wherein said PULLULAN further includes the properties of high adhesion, lubrication, and film forming abilities.

\* \* \* \* \*